US012616781B2

(12) United States Patent
Brohm-Schmitz-Rode et al.

(10) Patent No.: US 12,616,781 B2
(45) Date of Patent: May 5, 2026

(54) TUBULAR NONWOVEN STRUCTURE AS ACTIVE AGENT CARRIER FOR THE ATRAUMATIC TREATMENT OF HOLLOW ORGANS, AND A PROCESS FOR PRODUCING THE SAME

(71) Applicant: BVS—Best Vascular Solutions GmbH, Bonn (DE)

(72) Inventors: Andrea Brohm-Schmitz-Rode, Aachen (DE); Thomas Schmitz-Rode, Aachen (DE)

(73) Assignee: BVS—Best Vascular Solutions GmbH, Bonn (DE)

( * ) Notice: Subject to any disclaimer, the term of this patent is extended or adjusted under 35 U.S.C. 154(b) by 1264 days.

(21) Appl. No.: 17/337,090

(22) Filed: Jun. 2, 2021

(65) Prior Publication Data

US 2021/0379252 A1     Dec. 9, 2021

(30) Foreign Application Priority Data

Jun. 5, 2020    (DE) ..................... 10 2020 115 094.6
Jul. 6, 2020    (DE) ..................... 10 2020 117 801.8

(51) Int. Cl.
*A61L 31/16*          (2006.01)
*A61L 31/06*          (2006.01)
(Continued)

(52) U.S. Cl.
CPC ............... *A61L 31/16* (2013.01); *A61L 31/06* (2013.01); *A61L 2300/408* (2013.01);
(Continued)

(58) Field of Classification Search
CPC .... A61L 31/16; A61L 31/06; A61L 2300/408; A61L 2300/416; A61L 2300/43;
(Continued)

(56) References Cited

U.S. PATENT DOCUMENTS

| | | | |
|---|---|---|---|
| 5,443,495 A | 8/1995 | Buscemi et al. | |
| 5,507,770 A | 4/1996 | Turk | |
| 5,551,954 A * | 9/1996 | Buscemi ................... | A61F 2/88 |
| | | | 623/1.42 |
| 6,059,823 A | 5/2000 | Holman et al. | |

(Continued)

FOREIGN PATENT DOCUMENTS

| | | |
|---|---|---|
| DE | 102006020687 A1 | 2/2007 |
| DE | 102005056529 A1 | 5/2007 |

(Continued)

*Primary Examiner* — Yashita Sharma
*Assistant Examiner* — Jose H. Trevino, III

(57) ABSTRACT

A tubular nonwoven structure as an active agent carrier ("sleeve") for the atraumatic treatment of hollow organs, in particular applicable via a balloon catheter, as well as a method for the production thereof, wherein the sleeve is folded about a longitudinal sleeve axis in an initial state and is unfoldable in a final state for attachment to an inner wall of a hollow organ, the tubular sleeve is formed of first biodegradable polymer nanofibers and the folding of the sleeve is directed as pleating about a longitudinal sleeve axis, a medicinal active agent is incorporated into the first polymer nanofibers and/or is arranged in interspaces between the polymer nanofibers, and the first polymer fibers are formed such that the polymer fibers degrade over a period of 2 weeks to 3 months so that the active agent can be delivered to a hollow organ wall in this period of time.

18 Claims, 9 Drawing Sheets

(51) Int. Cl.

| | |
|---|---|
| *B29C 69/00* | (2006.01) |
| *B29L 31/00* | (2006.01) |
| *B33Y 10/00* | (2015.01) |
| *B33Y 80/00* | (2015.01) |

(52) U.S. Cl.

CPC ..... *A61L 2300/416* (2013.01); *A61L 2300/43* (2013.01); *A61L 2300/432* (2013.01); *A61L 2400/12* (2013.01); *B29C 69/008* (2013.01); *B29L 2031/7534* (2013.01); *B33Y 10/00* (2014.12); *B33Y 80/00* (2014.12)

(58) Field of Classification Search

CPC ........... A61L 2300/432; A61L 2400/12; A61L 31/048; A61L 31/10; A61L 31/148; B29C 69/008; B29L 2031/7534; B33Y 10/00; B33Y 80/00

See application file for complete search history.

(56) References Cited

U.S. PATENT DOCUMENTS

| | | | |
|---|---|---|---|
| 2002/0045930 A1 | 4/2002 | Burg et al. | |
| 2005/0090888 A1 | 4/2005 | Hines et al. | |
| 2005/0125053 A1 | 6/2005 | Yachia et al. | |
| 2008/0262594 A1 | 10/2008 | Morris | |
| 2010/0249946 A1 | 9/2010 | Lesh et al. | |
| 2015/0209299 A1* | 7/2015 | Xia ..................... | A61K 31/565 |
| | | | 424/443 |
| 2019/0046693 A1 | 2/2019 | Ahlering et al. | |

FOREIGN PATENT DOCUMENTS

| | | | |
|---|---|---|---|
| DE | 102012007640 | A1 | 10/2013 |
| DE | 102015104338 | A1 | 9/2016 |
| WO | 02076700 | A1 | 10/2002 |
| WO | 2016151035 | A1 | 9/2016 |

* cited by examiner

TUBULAR NONWOVEN STRUCTURE AS ACTIVE AGENT CARRIER FOR THE ATRAUMATIC TREATMENT OF HOLLOW ORGANS, AND A PROCESS FOR PRODUCING THE SAME

FIELD OF THE INVENTION

The present invention relates to a tubular sleeve and a system for atraumatic treatment of hollow organs and a method of fabrication.

The present invention relates to a tubular nonwoven structure (hereinafter also referred to as "sleeve") and a system for atraumatic treatment of hollow organs, as well as a method of producing the same.

BACKGROUND OF THE INVENTION

Stents are known for the scaffolding of constrictions (stenoses) in human hollow organs, such as blood vessels. A stent (vascular support) is a medical implant that can be inserted into a hollow organ. It is usually a tubular mesh structure made of metal or plastic. The stent is intended to support the affected section of a hollow organ and in this way keep it permanently open.

Usually, stents are delivered to the implantation site by means of a catheter or a balloon catheter. For this purpose, the stent can be arranged in a compressed state on a balloon catheter. The stent should have the smallest possible outer diameter in order to cause as little damage as possible to the corresponding hollow organ when it is introduced into the human and/or animal body. For this purpose, radial forces are usually applied to the stent, resulting in a concentric diameter reduction. Once the stent is positioned at the implantation site, the balloon catheter is inflated so that the stent expands concentrically.

However, the stent material may in some cases cause clot formation (thrombosis). Furthermore, mechanical stress during inflation of the balloon catheter may cause injury to the hollow organ wall of the hollow organ. The stent often leads to chronic irritation in the long term. The hollow organ wall reacts to this irritation with an overproduction of wall cells and so-called extracellular matrix (hyperplasia). Such vessel wall proliferation can be so severe that it leads to re-narrowing of the blood vessel (restenosis). Because of the thrombogenicity of the tears in the hollow organ wall and also of the stent material, drug anticoagulation treatment is often given to prevent clot formation. However, this therapy may have side effects. Therefore, a reduction of such medication would be desirable.

Furthermore, attempts are often made to reduce vessel wall proliferation by so-called "drug eluting stents". Such stents are usually coated with a polymer in which antiproliferative agents are incorporated or these stents are doped with such agents. The release of the antiproliferative agents at the site of implantation reduces the overproduction of wall cells. However, in some patients, these agents prevent the stent from growing into the wall of the vessel. After discontinuation of anticoagulation medication, so-called late thrombosis may occur, because the stent has not grown into the vessel wall, not at all or not completely.

To avoid the above problems, new stent concepts are being pursued, including so-called bioresorbable stents. These can be made of biodegradable metal alloys, e.g. with a high magnesium content, or of biodegradable polymers, e.g. polylactide. It is envisaged that such stents support the vessel wall for several months and are then be biodegraded by the body's own substances. In this way, the mechanical irritation of the vessel wall is also reduced and there should be less restenosis. According to initial studies, however, even with biodegradable stents, loading with antiproliferative agents cannot be dispensed with, because the excessive vascular wall reaction must be suppressed in the first few months after implantation.

Such devices and processes are described in DE 10 2012 007 640, WO 02 076 700 A1, U.S. Pat. No. 5,443,495 A1, DE 10 2006 020 687 A1, US 2005/0 090 888 A1, DE 2005 056 529, US 2002/0 045 930 A1, US 2005/0 125 053 A1, US 2008/0 262 594, U.S. Pat. Nos. 5,507,770 A, 6,059,823 A and US 2010/249946 A1.

The dilatation of constrictions (stenoses) of hollow organs using balloon catheters is an integral part of minimally invasive therapy. This applies in particular to the blood vessels. Within the framework of so-called endovascular therapy atherosclerosis-related constrictions and occlusions of blood vessels are treated by balloon dilatation.

Typically, a balloon catheter is inserted into the vascular system under imaging control. After placing the balloon in the area of the lesion to be treated, the balloon is expanded under high pressure. However, this standard treatment may be associated with serious complications. The balloon expansion injures the vessel wall. Typically, longitudinal tears occur in the vessel wall. This injury may result in clot (thrombus) adhesion in the first few days after treatment. In the following days up to a period of about three months, the blood vessel wall responds to the dilatation trauma with an exuberant wall reaction. Smooth muscle cells in the vessel wall are stimulated by the trauma and produce extracellular matrix ("intimal hyperplasia"). The associated increase in volume in the vessel wall leads to the reformation of a constriction (stenosis) and thus counteracts the treatment result. Even the implantation of a vascular support device (stent) to permanently widen the vessel cannot prevent this. A stent is a foreign body which, on the one hand, can have a clot-forming effect and, on the other hand, due to its rigidity, prevents the natural pulsatile motility of the stent-supplied vessel section and thus exerts a constant mechanical stimulus on the vessel wall. This stimulus can in turn lead to excessive production of vessel wall cells with tissue ingrowth through the stent struts and thus to the formation of a new stenosis.

Therefore, the stents commonly implanted today are coated with an "antiproliferative" agent that reduces cell stimulation and matrix production. In the case of balloon dilatation alone without stent implantation, balloon catheters are predominantly used today whose balloon is coated on the outside with a comparable active agent, which is intended to be transferred into the vessel wall during balloon dilatation. Usually, the coating consists of a homogeneous film-like coating of the outer balloon surface containing the active substance embedded in a carrier material (binder, "exipient"). The therapeutic goal is to deliver a therapeutic dose of drug into the vessel wall for the critical period of 6 weeks to a maximum of 3 months to suppress the overshooting vessel wall response (Katsanos et al, J Am Heart Assoc 2018).

In particular, WO 2016/151035 A1 describes a tubular sleeve for atraumatic treatment of hollow organs.

The purpose of the present invention is to provide a medical instrument for atraumatic treatment of hollow organs, which represents an alternative to the medical devices known from the prior art, such as stents, and which offers broader application possibilities.

A further purpose of the present invention is to provide an improved medical instrument for the atraumatic treatment of hollow organs and, in particular, to further develop a tubular sleeve known from WO 2016/151035 A1.

In addition, a method for production of such a medical instrument is to be provided.

SUMMARY OF THE INVENTION

According to the invention, a tubular nonwoven structure as an active agent carrier (called "sleeve" for short) for the atraumatic treatment of hollow organs, in particular for balloon dilatation, wherein the sleeve is folded about a longitudinal axis of the sleeve in an initial state and can be unfolded in a final state for attachment to an inner wall of a hollow organ, wherein the tubular sleeve is formed from at least first biodegradable polymer nanofibers and the folding of the sleeve is directed as a pleating about a longitudinal axis of the sleeve, wherein a medicinal active agent is incorporated into the first polymer nanofibers and/or is arranged in interspaces between the polymer nanofibers, and wherein the first polymer fibers are designed in such a way that they degrade as slowly biodegradable polymer nanofibers (PL) over an adjustable period of time of 2 weeks to 3 months, so that the active substance can be delivered to a hollow organ wall during this period of time.

In the context of the present invention, the term "biodegradable" (bio-decomposable) is understood to mean that contact of the polymer nanofibers or the polymer with body fluid and a hollow organ wall (specifically: blood and blood vessel wall) induces a decomposition or degradation process of this polymer. Here, according to the invention, it is provided that the medicinal agent is delivered to a hollow organ wall (especially: vessel wall) over the same adjustable period of time. Thus, the duration of the therapy can be adjusted relatively precisely.

For the main vascular application, it is particularly intended that the first fibers degrade within 2 weeks up to 3 months. For contraceptive applications, the fibers may be designed to degrade over a long period of time, from one year to 5 years, especially up to three years.

In known products for atraumatic treatment of hollow organs, especially for balloon dilatation, the outer surface of the balloon is impregnated with a mixture of a carrier polymer and an active agent, i.e. the active agent is delivered in the form of multiple particles (nanoparticles or microparticles or "microreservoirs" respectively). Thus, there is no coherent sleeve that is applied or released by means of a balloon catheter.

In US 2019/0046693 A1, for example, a homogeneous coating is provided that forms a plurality of microreservoirs that are in dispersed form in a lipophilic matrix on the outer surface of the balloon and are delivered to the vessel wall upon balloon deployment. Thus, a tubular sleeve in the sense of the present invention is not provided.

By being tubular, the sleeve of the present invention has an outer wall and an inner wall.

The tubular sleeve according to the invention is applied onto a balloon of a balloon catheter. By expanding the balloon in the blood vessel, it is deployed and adheres to the vessel wall. The sleeve is thus pressed with its outer wall against the hollow organ wall (especially: vessel wall) by the balloon unfolding in the hollow organ (especially: blood vessel). This results in an areal contact of the entire outer wall of the sleeve with blood during deployment, and after deployment and deflation of the balloon in an areal contact of the inner wall with blood, whereby the outer wall is in areal contact with the vessel wall. As the sleeve is loaded with a medical agent, the agent diffuses into the vessel wall. Drug delivery into the vessel wall continues until the sleeve has been biodegraded.

Furthermore, the sleeve can be designed in such a way that a "liner" function covers the longitudinal tears in the vessel wall that occur during balloon dilatation, thereby reducing thrombogenicity. Tears in the wall of the hollow organ caused by expansion or inflation of the balloon catheter can be excluded from direct contact with blood by the unfolded sleeve completely covering the lesion. In this way, the thrombogenicity, i.e., the tendency to blood clot formation in the area of the treated vascular lesion, is reduced.

Preferably, the folding of the tubular sleeve can be formed as pleating or the sleeve can be pleated. In the context of the present invention, pleating is understood to mean folding, winding and compressing of the tubular sleeve. By pleating, it is possible to reduce the outer diameter of the tubular sleeve in the non-defolded state. Optionally, an adhesive can be applied to the surface of the folded sleeve to stabilize the folding and thus maintain the small diameter during transport to the implantation site.

The folding of the sleeve is directed around a longitudinal sleeve axis, whereby the pleating and folding can take place both clockwise and counterclockwise. The pleating and folding is similar to that described in WO 02 076 700 A1 on the basis of a balloon catheter.

According to the invention, the tubular sleeve, implantable with the balloon dilatation, serves as a carrier for a defined dose of a medical agent, which can be safely and reliably brought into contact with a vessel wall by means of the deployed tubular sleeve.

The biodegradable polymer nanofibers deliver a therapeutically effective concentration of agent over a predetermined period of time while maintaining a relatively constant level of the agent in the vessel wall. Unlike systems without a tubular sleeve, there is no rapid drop in the concentration of the agent after balloon removal.

In contrast to a short-term balloon contact of the vessel wall with conventional drug-coated balloon catheters the implanted (therefore long-term contacting) tubular sleeve and the active agent bound therein thus prevent that a larger amount of the agent is washed off into the periphery of the vessel. The associated negative systemic side effects are thus reduced.

In the context of the present invention, a nonwoven structure is understood to be a structure of microfibers and/or nanofibers that forms a tubular fleece-like web. The wall thickness of the nonwoven tubular structure is less than 50 µm, preferably about 10 to 20 µm. In this context, the implanted sleeve should not impair the natural motility of the hollow organ wall (especially: vessel wall) due to its not too great inherent rigidity (i.e., it should not be as rigid as a conventional stent).

The active agent delivery via the degradation of the biodegradable polymer nanofibers covers the therapeutically required time phase with a therapeutically effective dose level. According to the invention, the biodegradation or the decomposition of the fibers and thus the release of the active agent should be completed when the critical phase is over, so that no permanent implant remains in the vessel.

By embedding the active agent in a lipophilic polymer component of the locally fixed sleeve, the wash-off of the agent from the vessel wall by the blood flow and the outflow to the periphery that occurs in known systems is significantly reduced.

There are interstitial spaces between the individual fibers. These interspaces form microcompartments as defined in WO 2016/151035 A1.

According to the invention, a tubular sleeve formed of multiple polymer nanofibers can be arranged on a balloon of a balloon catheter and is preferably foldable and expandable together with the balloon of the balloon catheter, whereby the sleeve detaches from the balloon during balloon expansion and is pressed against the hollow organ wall (especially: vessel wall), and adheres to the hollow organ wall (especially: vessel wall) after balloon deflation, and contains the active agent enclosed in a slowly degradable fiber component (PL), which in the course of its biodegradation (bio-decomposition) provides the therapeutically effective level of the active agent for a critical period in contact with the hollow organ wall (especially: vessel wall), and at the same time also seals the longitudinal cracks in the hollow organ wall (especially: vessel wall), which are typically formed after balloon dilation. In this way, the delivery of the active agent and its concentration over time can be optimally adjusted to the application.

After its production, the sleeve remains complete and whole for the period of storage of the balloon catheter on the balloon membrane until application, that means it is a single, self-consistent structural element, with a continuous tubular inner and outer wall, with micro-compartments formed between the fibers.

According to one embodiment, the tubular sleeve retains approximately its original tubular dimensionality after an initial body fluid or blood contact because of the low degree or absence of a rapidly degradable polymer nanofiber (PS) component.

The tubular sleeve may be formed from at least the first and second, preferably biodegradable, polymer nanofibers. Other biodegradable or non-biodegradable fibers may also be provided.

The second polymer nanofibers are formed from rapidly degradable polymer fibers (PS).

Preferably, only the slowly degradable polymer (PL) incorporates an active agent.

A medical active agent may also be incorporated into the second biodegradable polymer nanofibers or into further fibers, wherein the second polymer nanofibers are formed in such a way that the fibers degrade over a period of 1 second to 2 weeks, in particular 1 to 3 seconds to 10 minutes, preferably 3 seconds to 5 minutes, so that the active agent can be delivered to a hollow organ wall in this time period.

Preferably, an active agent is only incorporated into the slowly degradable polymer. An anticoagulant active agent such as heparin or an anticoagulant may also be incorporated into the rapidly degrading polymer (PS).

If two polymer solutions are provided for the production of the tubular nonwoven structure, which are sprayed (air spraying) or spun (electrospinning) simultaneously (via parallel nozzle arrangement or a coaxial nozzle arrangement with central channel and surrounding annular channel, also known as "core-shell nozzle"), then, for example, solution 1 consisting of PL:PS 80:20 (proportions in volume percent) can be mixed with the active agent Sirolimus, and solution 2, consisting of PL:PS 20:80, can be applied without active agent or mixed with an anticoagulant.

In the resulting sleeve, there is then a very small amount of active agent within the rapidly degradable polymer (second polymer, PS), which is accepted. The advantage is that the PS portion makes the fibers more adhesive and can have a protective colloid function.

The influence of the PS to PL ratio on the flake size is briefly shown below by way of example.

As an example, the following dependence of the flake size on the PS/PL mixing ratio can be determined for a specific PS polymer and a specific PL polymer:

PS: rapidly degradable polymer
PL: slowly degradable polymer

| | Mean flake size on contact with water in µm after | | | | |
|---|---|---|---|---|---|
| PS/PL in Vol.% | 1 minute | 1 hour | 1 day | 1 week | 1 month |
| 0/100 | >200 | 100 | 90 | 70 | 30 |
| 20/80 | >100 | 80 | 70 | 50 | 20 |
| 50/50 | 50 | 40 | 35 | 30 | 15 |
| 80/20 | 35 | 30 | 25 | 15 | 10 |

For a PS content of 0 (100 vol. % PL), an average or mean flake size immediately after water or serum contact is greater than 200 µm and after one week is approximately 70 µm. For a PS content of 80 vol. % (20 vol. % PL), the average flake size immediately after water or serum contact is about 35 µm and after one week about 15 µm, etc.

The foregoing describes only by way of example the technical effect of the present invention for a specific PS polymer and a specific PL polymer.

By changing the parameters polymer type, polymer chain length (molecular weight) and type of side groups, the size range for the average flake size can be strongly influenced.

The rapidly degradable polymer is preferably very hydrophilic, while the slowly degradable polymer has significantly more lipophilic properties. The rate of degradation depends on the type of polymer (for example, in the case of PLGA—poly(lactide-co-glycolide) by the ratio of GA to LA (a higher content of LA causes a reduction in hydrophilicity and therefore leads to slower dissolution), the molecular chain length (a high molecular weight or a longer chain length causes slower dissolution), and the hydrophilicity of the side groups (e.g., the methyl side groups in PLA have a hydrophobic effect and thus delay dissolution, or in the case of PLGA a hydrophilic carboxyl group leads to faster dissolution than an ester group).

Thus, the degradation kinetics can be adjusted in body fluid or blood, depending not only on the geometry (fiber dimensions and nonwoven texture) but also on the type of polymer, molecular weight, and type of side chains (hydrophilic or hydrophobic).

The slowly degradable and the rapidly degradable polymer nanofibers can be blended in the tubular sleeve in a ratio of 90 vol-% to 10 vol-% or of 80 vol-% to 20 vol-% or of 70 vol-% to 30 vol-% or of 60 vol-% to 40 vol-% or of 50 vol-% to 50 vol-% or of 40 vol-% to 60 vol-% or of 30 vol-% to 70 vol-% or of 20 vol-% to 80 vol-% or of 10 vol-% to 90 vol-%, respectively.

Since, according to a preferred embodiment, a particularly rapidly biodegradable component PS is provided, after deployment of the sleeve, rapid disintegration of the sleeve begins into multiple platelets or flakes or microflakes adhering to the hollow organ wall in an overall sleeve-like tubular arrangement.

This embodiment of the implanted sleeve, which provides for rapid fragmentation into microflakes by dissolution of the rapidly dissolving component, can additionally prevent small side branches in the implantation segment from being obstructed, because no continuous planar coverage is formed in the orifice region of the side branches due to side branch perfusion.

In particular, a ratio of slowly and rapidly degradable polymer nanofibers in the tubular sleeve of 50 vol % to 50 vol % is universally applicable. The geometry of the fibers with PS:PL 50:50 is shown in FIG. 4. The embodiment shown in FIG. 5 has a very small PS content and shows disintegration into relatively large fragments ("flakes") after water contact.

In particular, a ratio of rapidly to slowly degradable polymer nanofibers in the tubular sleeve of PS=70 vol-% to PL=30 vol-% is preferred for small vessels. A ratio of 70 vol-% PS and above corresponds to a large PS fraction in the context of the present invention.

In particular, a ratio of rapidly to slowly degradable polymer nanofibers in the tubular sleeve of PS=30 vol-% to PL=70 vol-% is preferred for large vessels. A ratio of 30 vol-% PS and below corresponds to a small PS fraction in the context of the present invention.

The greater the fraction of rapidly degradable polymer nanofibers PS in the tubular sleeve, the smaller the flakes will be. Therefore, a high proportion of rapidly degradable polymer nanofibers is particularly suitable for small vessels, as small flakes can adapt better to the anatomy of small vessels.

Thus, this embodiment is characterized by the fact that the rapid dissolution of the corresponding fibers (within a few seconds up to 5 minutes) causes a disintegration of the previously consistent cylindrical sleeve into multiple "flakes" or "microflakes", which are flat and adhere to the hollow organ wall.

The resulting flakes consist predominantly of the slowly degradable component containing the active agent, while the rapidly degradable component dissolves the cohesion of the formerly coherent sleeve as a single part and induces the disintegration of the sleeve into multiple parts ("microflakes").

Preferably, a single flake has an areal dimension of 10 to 30 μm and a thickness of 5 to 10 μm.

The initial disintegration kinetics of the sleeve into multiple microflakes in a tubular overall arrangement is thus essentially determined by the proportion and arrangement of the rapidly degradable component. Thus, depending on the proportion and arrangement of the rapidly degradable component, a shape transition is effected after body fluid or blood contact, from coherent cylindrical or tubular to multiple microflakes, which are present separately in each case, but as a whole are in a tubular overall arrangement.

Another option would be a shape transition after blood contact from tubular microporous (e.g. multiple pores <20 μm) to tubular macroporous (multiple pores >20 μm), i.e. large pores, but without immediately dissolving the cohesion of the sleeve. This means that there is no immediate disintegration of the sleeve with the formation of multiple individual particles (microflakes), but only in the further course of the degradation process.

The biocompatible polymer of polymer nanofibers can be made of polymers based on lactic acid (polylactide, PLA), glycolic acid (polyglycolide, PGA) and their copolymers (poly(lactide-co-glycolide), —PLGA), as well as poly(ε-caprolactone), polyethylene glycol, polyethylene oxide, polysebacic acid, po-ly(trimethylene carbonate), poly(ethylene-co-vinyl acetate), poly(1,5-dioxepan-2-one), polyvinylpyrrolidone (PVP), poly-p-dioxanone (PPDX) and their compounds and copolymers or mixtures thereof, the polymer nanofibers preferably having a fiber diameter smaller than one micrometer and preferably in the range from 300 to 2000 nm and in particular in the range from 500 to 1000 nm. In the context of the present invention, the polymer nanofibers may also have a diameter of up to 3 micrometers.

The tubular sleeve may have a radial support layer, wherein the radial support layer is formed by higher strength polymer nanofibers and/or by an additional polymer layer.

The radial support layer may be formed, for example, as a laser-cut tubular biodegradable polymer semi-finished product or as a layer formed by means of Melt Electrospinning Writing (MEW).

Adhesion to the hollow organ wall can already be strengthened by the inherent radial stiffness of the sleeve (without support layer) after unfolding. This can also be achieved by combination with the mechanically stronger radial support layer (a kind of support scaffold), which degrades only slowly.

At least one outer circumferential wall of the sleeve can have adhesive properties and/or be provided with a coating such that the circumferential wall adheres to an inner wall of a hollow organ during unfolding.

Preferably, one of the two polymer components has tacky or adhesive properties, which promotes adhesion to the hollow organ wall. Thus, the adhesion of the sleeve to the hollow organ wall can be strengthened by an adhesive polymer component.

For larger hollow organ diameters, adhesion to the hollow organ wall can also be improved by increasing the radial support force as shown above.

When the balloon is deflated, the outer surface of the sleeve adheres to the wall of the hollow organ (due to the sticky adhesive nature of the material) and complete detachment of the sleeve from the balloon membrane causes the entire inner surface of the sleeve to come into contact with body fluid or blood.

Even detachment from the balloon membrane can be improved by applying a release coating to the balloon membrane beforehand.

The tubular sleeve can have a wide variety of diameters and lengths, matched to the geometry of the hollow organ lesion to be treated. For example, a version with a diameter of 5 mm in the expanded final state and a length of 40 mm can have a wall thickness of 20-30 μm.

A method of producing a tubular sleeve for atraumatic treatment of hollow organs, in particular for application via balloon dilatation, is described below. The method comprising the following steps:

Providing a mixture of at least one polymer dissolved in a solvent and a medical active agent, applying the mixture layer-by-layer to a cylindrical support to form a tubular nonwoven of polymer nanofibers, pleating and folding the nonwoven after removal of the support and winding the pleats in the same direction about a central axis, mounting the pleated and folded nonwoven sleeve onto the folded and wound balloon membrane of a balloon catheter or layer-by-layer application of the mixture to form a tubular nonwoven sleeve of polymer nanofibers directly onto the expanded balloon membrane of a balloon catheter, the balloon having been previously provided with a separation layer, and folding and coiling the nonwoven sleeve together with the deflated balloon membrane around the balloon catheter shaft.

The individual polymer nanofibers adhere to each other during the production process: cohesion, shape stability and mechanical properties result from the overall consistency of the multiple individual fibers adhering to each other.

For production by spraying (air spraying) or by spinning in an electric field (electrospinning) or by a combination thereof (electrostatic air spraying), substances with sufficiently high vapor pressure such as chloroform, acetone, methanol, heptane, tetrahydrofuran, and others are suitable as solvents.

A first slowly degradable polymer may be dissolved in a first solvent, or solvent mixture of two or more solvents, and a second rapidly degradable polymer may be dissolved in the first solvent or in a second solvent, or solvent mixture of two or more solvents.

A protective colloid may be added to the mixture to enhance mixing and prevent deposition of the water-in-soluble medicinal agent, the protective colloid preferably being the rapidly degradable polymer.

The amount of protective colloid may be 10 to 20% by volume in the mixture and at the same time later support or improve the adhesion of the microflakes to the vessel wall.

The application of the solution to the cylindrical support or directly to the balloon can be done by spraying with an air jet (Air Spraying) or by spinning in an electric field (Electrospinning) or by a combination thereof (Electrostatic Air Spraying) and/or by dipping in a solution (Dip Coating) and/or by applying a continuous melt strand (Melt Electrospinning Writing) or can be applied discontinuously by 3D printing.

Typically, just one solution deposition process is provided. However, if technically feasible, combinations of the above processes may also be possible.

A separation layer can be applied to the carrier before the blend is applied. Suitable separation layers include hemocompatible, readily water-soluble polymers or sugar compounds.

The active agent can also be mixed in a polymer (slowly degrading—PL) solvent solution and applied to the outside of the nonwoven by dip coating. After evaporation of the solvent, the polymer PL with the active agent attaches to the fibers of the nonwoven, partially filling the microcompartments between the fibers. The nonwoven can preferably consist purely of rapidly degrading polymer PS or a PL/PS blend.

Prior to pleating and folding, intermittent longitudinal slits can be made in the sleeve in the course of the subsequent folding edges to facilitate folding and to bring about the desired pleating and folding course on the surface of the sleeve and the uniform distribution of the folding edges on the circumference. These longitudinal slits can preferably be created by laser cutting.

The carrier can be a cylindrical carrier body or an inflated balloon.

Direct deposition on a balloon is preferred. For this purpose, a separation layer is first applied to the inflated balloon membrane of a balloon catheter. The sleeve is then deposited on top of the separation layer. The tubular sleeve can be pleated and folded together with the balloon of the balloon catheter around the catheter shaft.

In particular, according to the invention, a system for atraumatic treatment of hollow organs is provided comprising a balloon catheter and the tubular sleeve according to the invention.

Moreover, in this system, an outer protective coating may be arranged on the sleeve in the initial state.

Such a film-like protective coating prevents blood contact and thus prevents thrombus formation during sleeve insertion. At the implantation site, the protective coating can then be removed by retraction or by deployment-induced tearing. In addition, stability of the folding of the sleeve for transport on the balloon catheter can be supported by adhesive surface treatment of the outer surface of the sleeve.

Furthermore, medical and therapeutic methods for treating hollow organs with a nonwoven structure and system disclosed above are provided.

The active agent loading of the sleeve as an active agent carrier depends on the site of action (hollow organ) and the disease. The medical agent may include one or more of the following.

To reduce an excessive wall reaction (intimal hyperplasia) in blood vessels, in particular in arteries, limus derivatives (e.g. sirolimus) or paclitaxel (PTX) can be provided as a medical active agent.

Limus derivatives seem to have a much more favorable biological effect than paclitaxel. However, they are difficult to transfer into the vessel wall with conventionally coated balloons by a single short balloon contact, as they adhere much more poorly than paclitaxel crystals that are pricked into the vessel wall. They require significantly more contact time for effective transfer into the vessel wall. In the case of the deployed and attached sleeve, the contact time with the vessel wall corresponds to the lifespan of the sleeve until it is degraded. At the same time, the transferred sleeve is also a guarantee of a specific amount of drug transferred (which is imponderable with one-time balloon contact with conventional drug coated balloon systems) and it holds the drug better at the site of action (with conventional balloon transfer, a large part of the transferred particles is washed down with the bloodstream to the periphery).

For use in blood vessels, the implanted sleeve should thus serve in particular as a carrier for antiproliferatives like limus derivatives and thus ensure their complete transfer with a longer-term contact to the vessel wall.

In the case of application of the sleeve as a fallopian tube active agent carrier with contraceptive effect, long-term stable depot gestagens, such as etonogestrel, levonorgestrel or a suitable antiprogesterone, such as mifepristone or a spermicide, such as nonoxinol 9 can be provided as active agents. In principle, application with a contraceptive agent in the region of the ductus deferens (vas deferens) is also possible.

For the therapy of carcinomas in hollow organs, e.g. in the bile ducts, cytostatic agents such as mitomycin, capecitabine or methotrexate (MTX) can be provided as medicinal agents for the sleeve. Other possible applications of the sleeve include other hollow organs such as the pancreatic duct, the urinary tract, lymphatic vessels such as the thoracic duct, the tracheobronchial system, the nasolacrimal duct, the eustachian tube, or even the gastrointestinal tract.

BRIEF DESCRIPTION OF THE DRAWINGS

The invention is described in more detail below with reference to the embodiments shown in the figures. These are shown in.

DETAILED DESCRIPTION OF THE PREFERRED EMBODIMENTS

Figure 1:
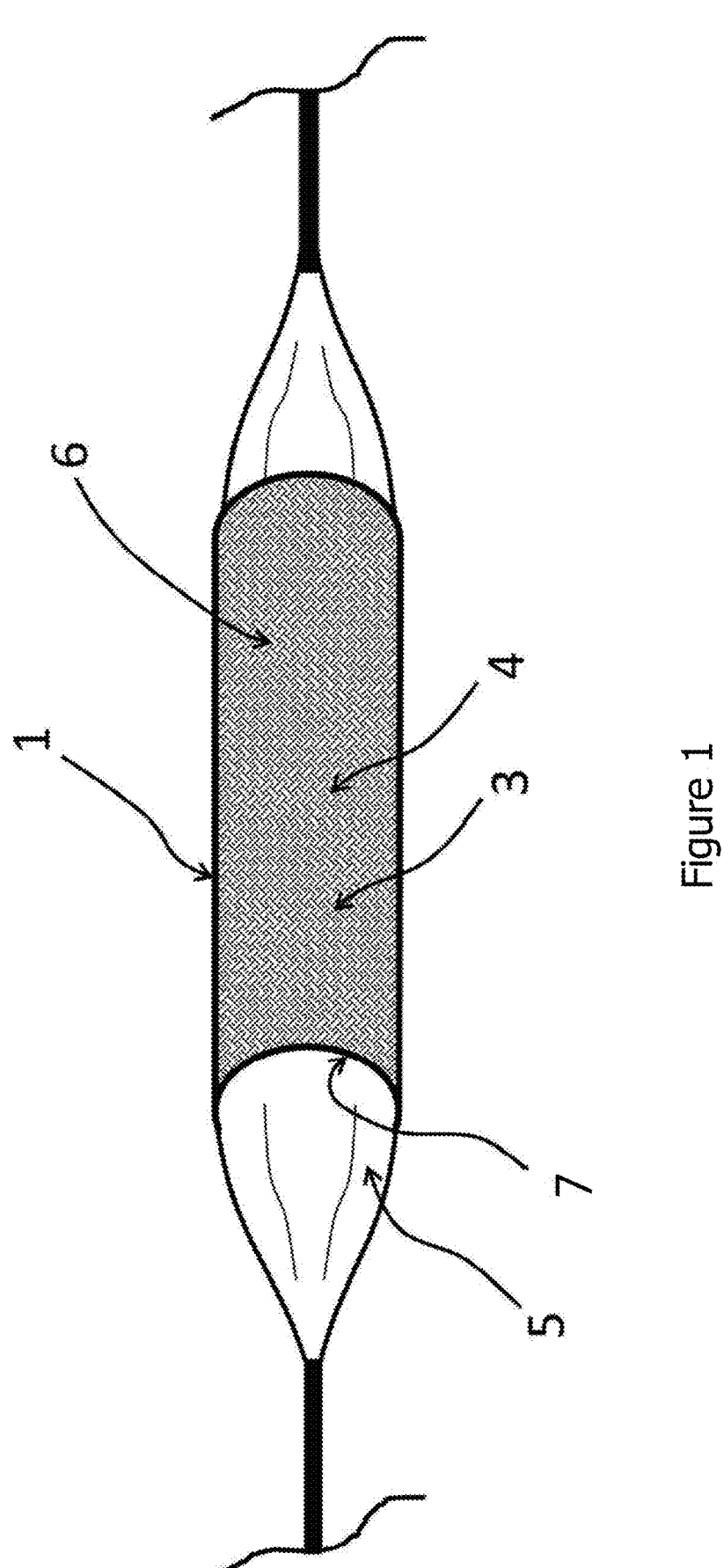
FIG. 1 is a schematic representation of a deployed tubular nonwoven structure ("sleeve"), arranged on an inflated balloon catheter, according to the present invention.
Figure 2:
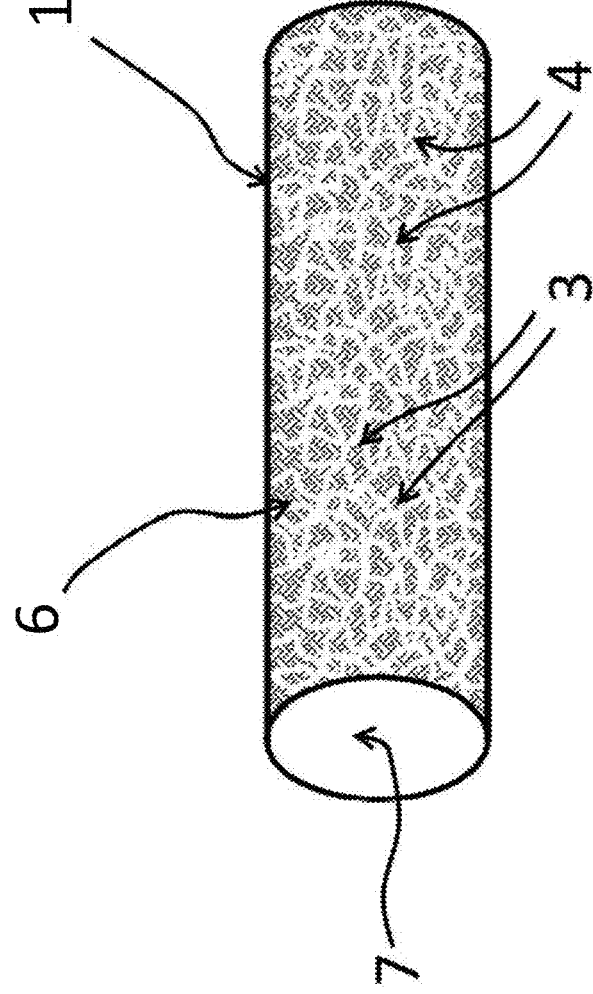
FIG. 2 is a schematic representation of the nonwoven structure after its release from the balloon catheter, the sleeve having been in contact with blood for minutes to hours, associated with the onset of disintegration into multiple microflakes.
Figure 3:
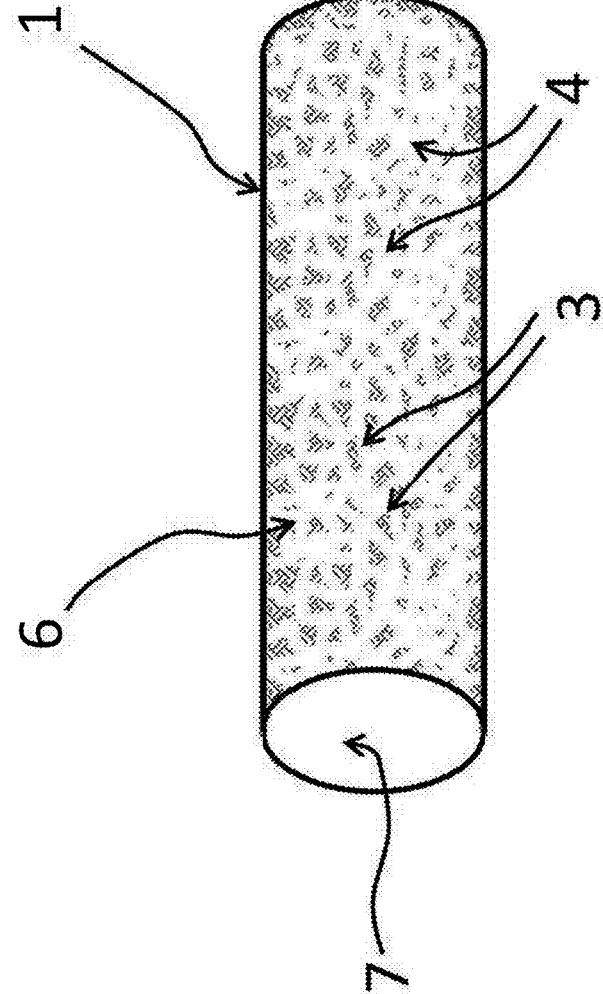
FIG. 3 is a schematic representation of the nonwoven structure after several days to weeks, such that multiple microflakes have formed in an overall cylindrical configuration.

According to the invention, a tubular nonwoven structure 1 or sleeve is provided as an active agent carrier for atraumatic treatment of hollow organs 2, in particular for balloon dilatation (FIGS. 1-3 and 6-9).

According to one embodiment, the tubular nonwoven structure 1 is formed of at least first biodegradable polymer nanofibers 3 and second biodegradable polymer nanofibers 4.

The first polymer nanofibers 3 are formed of a slowly degradable polymer (PL). The second polymer nanofibers 4 are formed from a rapidly degradable polymer (PS).

In the context of the present invention, it may also be provided that the first polymer nanofibers 3 are formed from the rapidly degradable polymer (PS) and the second polymer nanofibers 4 are formed from the slowly degradable polymer (PL). Further third and/or fourth degradable polymer nanofibers may also be formed from the rapidly degradable polymer (PS) or from the slowly degradable polymer (PL).

A degradation time of the slowly degradable polymer 3 (PL) is approximately 1 week or 2 weeks to 3 months or 6 months. For contraceptive applications, the fibers 3 (PL) may be designed to degrade over a long period of time, from one year to 5 years in particular to three years. A degradation time of the fast degradable polymer 4 (PS) is about 1 second or 30 seconds to 1 minute or up to 5 minutes or up to 10 minutes or up to one week.

The biocompatible polymer of the polymer nanofibers can be made of polymers based on lactic acid (polylactide, PLA), glycolic acid (polyglycolide, PGA) and their copolymers (poly(lactide-co-glycolide), —PLGA), as well as poly(ε-caprolactone), polyethylene glycol, polyethylene oxide, polysebacic acid, po-ly(trimethylene carbonate), poly (ethylene-co-vinyl acetate), poly(1,5-dioxepan-2-one), polyvinylpyrrolidone (PVP), poly-p-dioxanones (PPDX) and their compounds and copolymers or mixtures thereof, the polymer nanofibers preferably having a fiber diameter in the range from 300 to 2000 nm and in particular in the range from 500 to 1000 nm.

The wall thickness of the nonwoven structure is less than 50 μm, preferably the wall thickness is about 10 to 20 μm.

The slowly and the rapidly degradable polymer nanofibers may be present in the tubular sleeve in a ratio of 90 vol-% to 10 vol-%, or of 80 vol-% to 20 vol-%, or of 70 vol-% to 30 vol-%, or of 60 vol % to 40 vol % or of 50 vol % to 50 vol % or of 40 vol % to 60 vol % or of 30 vol % to 70 vol % or of 20 vol % to 80 vol % or of 10 vol % to 90 vol %.

Figure 4:
FIG. 4 is a microscopic image of the fiber texture of the nonwoven at a ratio of PS to PL of 50:50 vol % in a solution applied by a spraying method.

Universally applicable and provided according to this embodiment is in particular a ratio of slowly and rapidly degradable polymer nanofibers of 50 vol-% to 50 vol-% (FIG. 4).

In particular, a ratio of fast to slow degradable polymer nanofibers in the tubular sleeve of 70 vol % to 30 vol % is preferred for small blood vessels with a diameter of 1-5 mm.

Preferred for large blood vessels with a diameter of 5-20 mm is in particular a ratio of fast to slow degradable polymer nanofibers in the tubular sleeve of 30 vol-% to 70 vol-%.

One or both polymer components exhibit tacky/adhesive properties, promoting adhesion to the hollow organ wall.

The nonwoven structure 1 is folded about a longitudinal sleeve axis around the balloon of the balloon catheter 5 in a folded state (not shown). The folding of the sleeve is formed as a pleating directed around a sleeve longitudinal axis.

In a final state, the nonwoven structure 1 is formed to adhere to an inner wall of a hollow organ 2.

A medical active agent (not shown) is incorporated into the first polymer nanofibers 3 and accommodated in the interspaces between the polymer nanofibers.

Because the sleeve is tubular, it has an outer wall 6 and an inner wall 7.

The tubular sleeve can have a wide range of diameters and lengths to suit the geometry of the vessel lesion to be treated. For example, a version with a diameter of 5 mm in the expanded final state and a length of 40 mm can have a wall thickness of 20-30 μm.

A method of producing a tubular sleeve for atraumatic treatment of hollow organs, in particular for implantation by balloon dilatation, is described below. The method comprises the following steps:

Providing a mixture of at least one polymer dissolved in a solvent and a medicinal active agent, applying the mixture layer by layer to a cylindrical support to form a tubular nonwoven of polymer nanofibers, pleating and folding the nonwoven after removal of the support and winding the folds in the same direction about a central axis, applying the folded nonwoven to the folded and wound balloon membrane of a balloon catheter or applying the mixture to form a tubular nonwoven of polymer nanofibers directly to the outer surface of an expanded balloon of a balloon catheter in layers, the balloon having been previously provided with a separation layer, and pleating, folding and coiling the nonwoven together with the deflated balloon membrane around the balloon catheter shaft.

The individual fibers stick together during the production process: cohesion, shape stability and mechanical properties result from the overall consistency of the multiple individual fibers adhering to each other.

For production by spraying (air spraying) or by spinning in an electric field (electrospinning) or by a combination thereof (electrostatic air spraying), substances with sufficiently high vapor pressure such as chloroform, acetone, methanol, heptane, tetrahydrofuran, and others are suitable as solvents.

A first slowly degradable polymer may be dissolved in a first solvent or a solvent mixture of two or more solvents, and a second rapidly degradable polymer may be dissolved in the first solvent or in a second solvent or a solvent mixture of two or more solvents.

A protective colloid may be added to the mixture to enhance mixing and prevent deposition of the water-in-soluble medical active agent, the protective colloid preferably being the rapidly soluble polymer.

The application of the solution to the cylindrical support can be done by spraying with an air jet (air spraying) or by spinning in an electric field (electrospinning) or by a combination thereof (electrostatic air spraying) and/or by dipping in a solution (dip coating) and/or by applying a continuous melt strand (melt electrospinning writing) or discontinuously by means of 3D printing (additive manufacturing).

Normally, just one method is provided for applying the solution. However, if technically feasible, combinations of the above processes may also be possible.

A separation layer is applied to the substrate before the solution with the mixture is deposited. Suitable separation layers include hemocompatible, readily water-soluble polymers and sugar compounds.

The active agent can also be mixed in a polymer (slow degrading—PL) solvent solution and applied to the outside of the nonwoven by dip coating. After evaporation of the solvent, the polymer PL with the active agent attaches to the fibers of the nonwoven, partially filling the microcompartments between the fibers. The nonwoven can preferably consist purely of rapidly degrading polymer PS or a PL/PS blend.

Intermittent longitudinal cuts can be made in the sleeve prior to folding. The folding of the nonwoven can be facilitated by intermittent longitudinal slits in the course of the folding edges. These longitudinal slits can preferably be created by laser cutting.

The carrier can be a cylindrical carrier body or an inflated balloon.

Direct deposition on a balloon is preferred. For this purpose, a separation layer is first applied to the inflated balloon membrane of a balloon catheter. The sleeve is then deposited on top of the separation layer.

The tubular sleeve is folded around the catheter shaft together with the balloon of the balloon catheter.

In particular, according to the invention, a system for atraumatic treatment of hollow organs is provided which comprises a balloon catheter and the tubular sleeve according to the invention.

Moreover, in this system, an outer protective coating may be arranged on the sleeve in the initial state.

The tubular sleeve according to the invention is deposited on a balloon of a balloon catheter. By expansion of the balloon in the hollow organ (especially: blood vessel), it is deployed and adheres to the hollow organ wall (especially: vessel wall). The outer wall of the sleeve is thus pressed against the wall of the hollow organ (especially the vessel wall) as the balloon unfolds in the hollow organ (especially the blood vessel). Unfolding results in a areal contact of the entire outer wall of the sleeve with body fluid (especially: blood) during deployment, and an areal contact of the inner wall with body fluid (blood) after release and balloon deflation, whereby the outer wall is in areal contact with the hollow organ wall (vessel wall). Since the sleeve is loaded with a medical active agent, the active agent diffuses into the hollow organ wall (vessel wall). The active agent is released until the sleeve has been biodegraded.

Furthermore, the sleeve can be designed in such a way that the longitudinal wall tears formed during balloon dilatation are covered by a "liner" function, for example, in order to reduce thrombogenicity in the blood vessel. Tears in the wall of the hollow organ caused by expansion or inflation of the balloon catheter can be excluded from direct contact with body fluid (blood) by the unfolded sleeve completely covering the lesion. In this way, thrombogenicity, i.e. the tendency to form blood clots in the area of the treated vascular lesion, is reduced when applied in a blood vessel.

According to the invention, a tubular sleeve formed of multiple micro-nano-fibers can be arranged on a balloon of a balloon catheter and is preferably foldable and expandable together with the balloon of the balloon catheter, whereby the sleeve detaches from the balloon during balloon expansion and is pressed against the hollow organ wall, and adheres to the hollow organ wall after balloon deflation, and contains the active agent enclosed in a slowly degradable fiber component (PL) which, in the course of its biodegradation (bio-decomposition), provides the therapeutically active agent level for a critical period in contact with the hollow organ wall, and at the same time also seals the longitudinal cracks in the hollow organ wall formed after balloon dilatation. In this way, the release of the active agent and its concentration over time can be optimally adjusted to the application.

In a preferred embodiment, the provision of particularly rapidly biodegradable components means that after the balloon is released and adheres to the wall of the hollow organ, the sleeve begins to disintegrate rapidly into multiple plates or flakes or microflakes in a generally sleeve-shaped arrangement.

Thus, this embodiment is characterized by the fact that the rapid decomposition of the corresponding fibers (within a few seconds up to 5 minutes) causes a disintegration of the formerly consistent cylindrical sleeve into multiple "flakes" (=microparticles or "microflakes"), which are flat and adhere to the hollow organ wall.

The resulting flakes consist mainly of the slowly degradable component, which contains the active agent, while the rapidly degradable component dissolves the cohesion of the formerly coherent sleeve as a single part and induces the disintegration of the sleeve into multiple parts ("microflakes").

Preferably, a single flake has a areal extent of 10 to 30 μm and a thickness of 5 to 10 μm.

The nonwoven structure or system according to the invention is intended for the following medical and therapeutic procedures.

The active agent loading of the active agent carrier depends on the site of action (hollow organ) and the disease. The medically active agent may comprise one or more of the following.

For the reduction of an excessive wall reaction (intimal hyperplasia) in blood vessels, especially in arteries, limus derivatives (e.g. sirolimus) or paclitaxel (PTX) can be provided as a medicinal agent.

Limus derivatives have a much more favorable biological effect than paclitaxel. However, they are difficult to transfer into the vessel wall with conventionally coated balloons by a single short balloon contact, as they adhere much more poorly than paclitaxel crystals that are pricked into the vessel wall. They also require significantly more contact time for effective transfer into the vessel wall. In the case of the implanted sleeve, the contact time with the vessel wall is equal to the sleeve's lifetime until it is degraded. At the same time, the transferred sleeve is also a guarantee for the transferred amount of active agent (which is imponderable with one-time balloon contact with conventional systems) and it holds the active agent better at the site of action (with conventional balloon transfer, a large part of the transferred particles are washed into the periphery with the blood-stream).

For use in the vascular system, the implanted sleeve should thus serve in particular as a carrier for antiprolifera-tives like limus derivatives and thus ensure their complete transfer with longer-term contact with the vessel wall.

The main area of application is in the arteries, especially in the upper and lower leg, but also in the coronary vessels. While the femoral vessels still have diameters of up to 7 mm, the vessels in the lower leg and the coronary vessels with their branches have diameters of 5-2 mm. Application in the venous system or in hemodialysis shunts is also considered.

For use as a fallopian tube active agent carrier with long-term contraceptive effect, long-term stable depot gesta-gens, such as etonogestrel, levonorgestrel or a suitable antiprogesterone, such as mifepristone or a spermicide, such as nonoxinol 9 can be provided as medicinal active agents.

For the therapy of carcinomas in hollow organs, e.g. in the bile duct system, cytostatic agents such as mitomycin, capecitabine or methotrexate (MTX) can be provided for the sleeve as the active medicinal agent.

Figure 7:
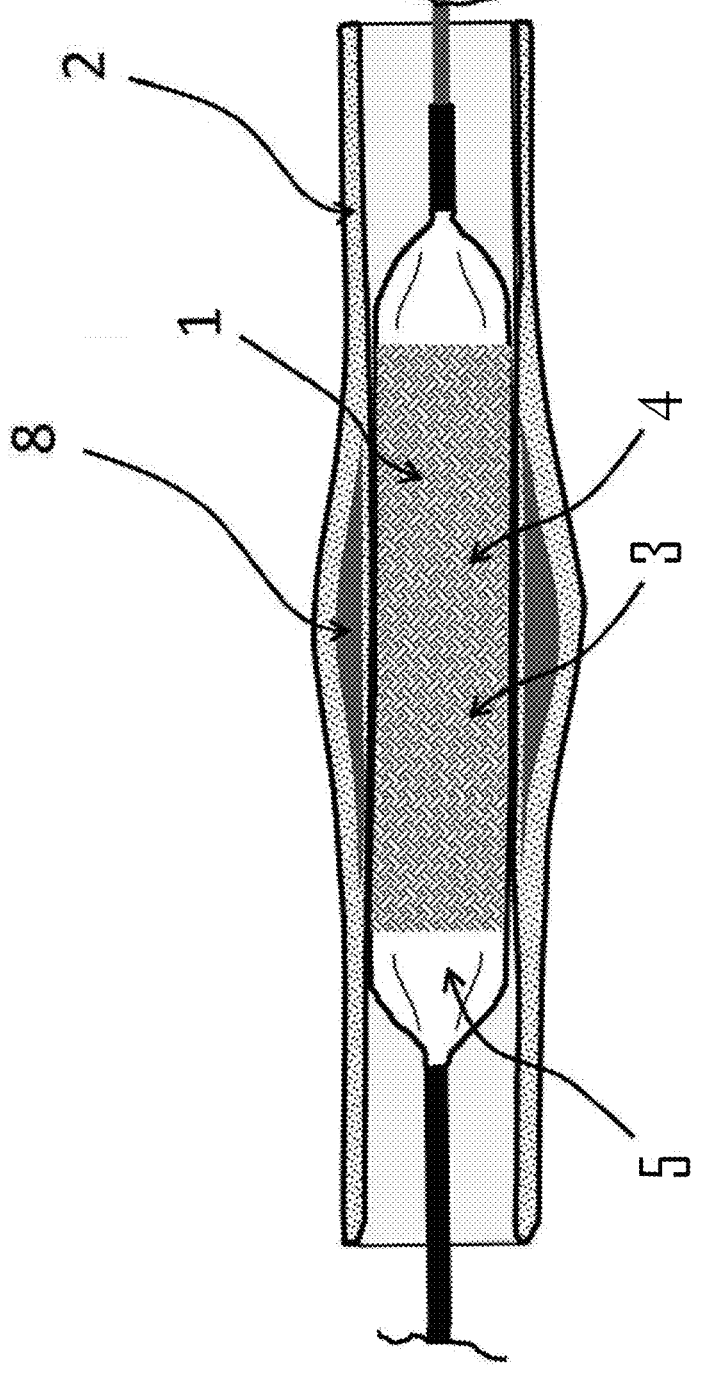
FIG. 7 is a schematic representation of the system according to the invention during balloon dilatation and the associated deployment of the sleeve.

After production, the nonwoven structure remains com-plete and integral (=consistent) for the period of storage of the balloon catheter on the balloon membrane until appli-cation, with a coherent cylindrical inner and outer surface (FIGS. 1 and 7).

At the moment of balloon deployment during application in the patient, an areal contact of the entire outer surface of the sleeve (and after release also of the inner surface) with body fluid or blood occurs.

As a result of the balloon deployment in the hollow organ (especially: blood vessel), the outer surface of the sleeve is pressed against the hollow organ wall (especially: vessel wall) (FIG. 7).

Figure 8:
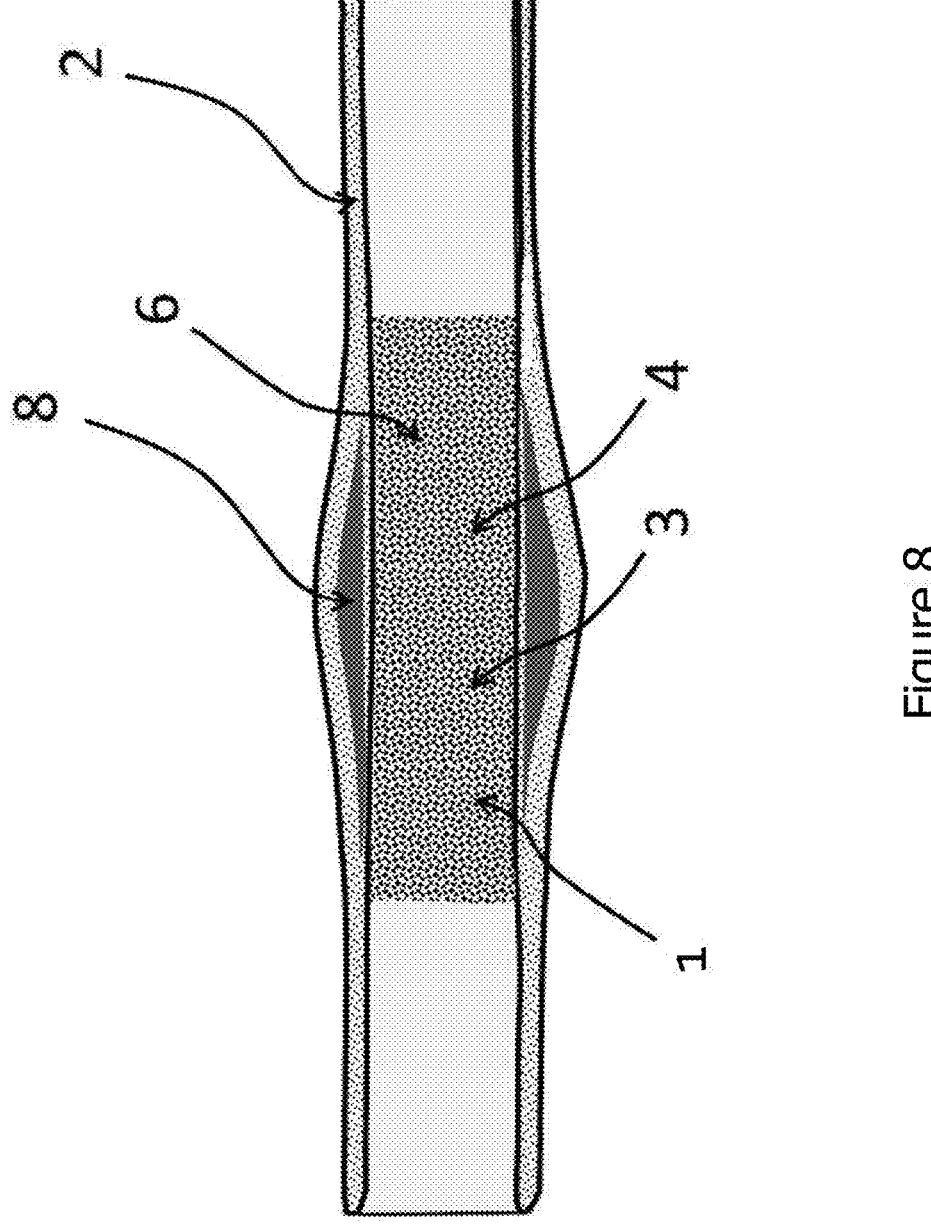
FIG. 8 is a schematic representation of the nonwoven structure attached to a vessel wall after balloon removal.
Figure 9:
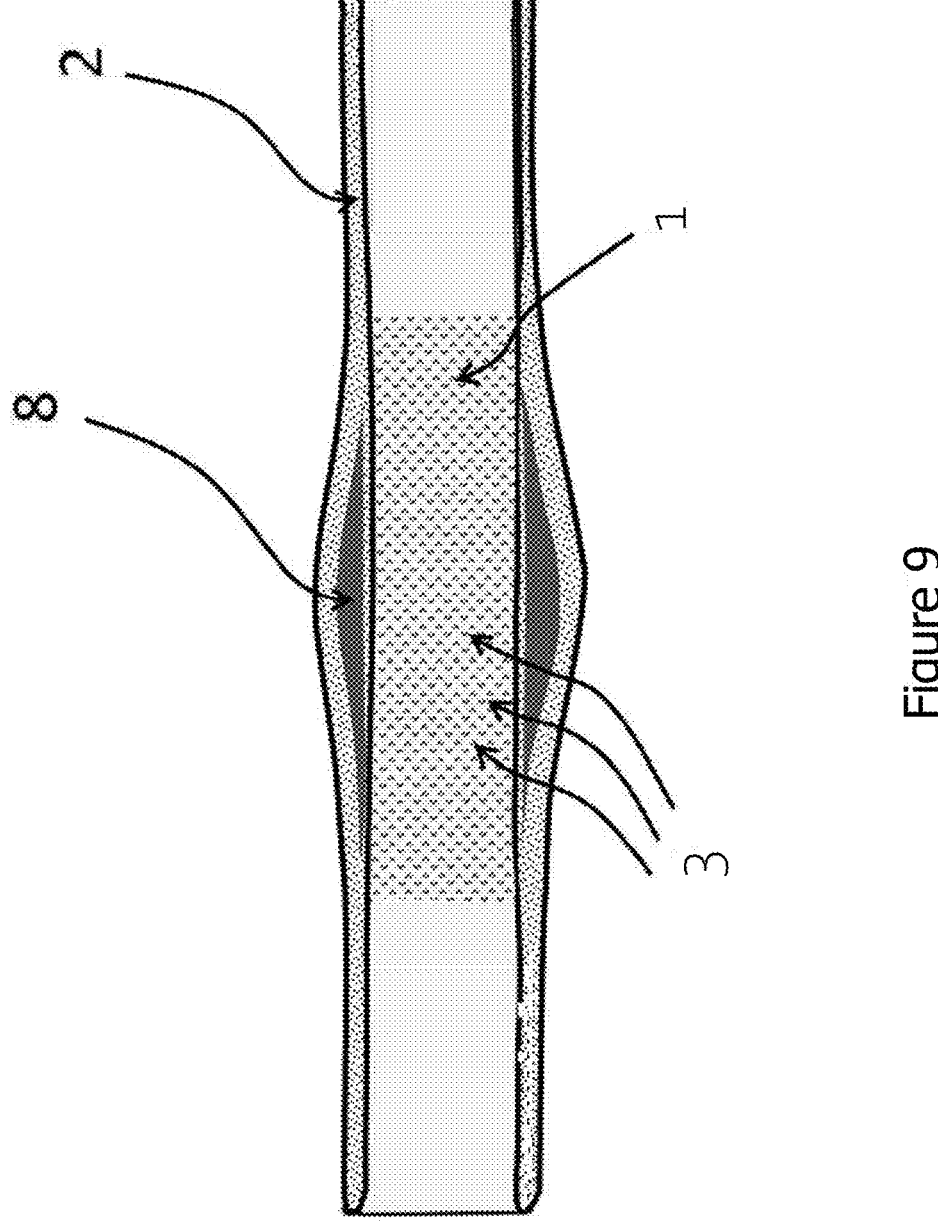
FIG. 9 is a schematic representation of the nonwoven structure a few hours to days after release in the state of increasing degradation and disintegration, associated with decomposition into multiple flakes.

When the balloon is deflated, the outer surface of the sleeve adheres to the wall of the hollow organ (due to the sticky adhesive nature of the material) and complete detach-ment of the sleeve from the balloon membrane results in areal contact of the entire inner surface of the sleeve with body fluid or blood (FIGS. 8 and 9).

Adhesion to the vessel wall can be enhanced by radial inherent stiffness of the sleeve after deployment.

Homogeneous detachment from the balloon membrane can be improved by prior application of a release layer to the balloon membrane.

The wetting of the inner and outer surface with body fluid or blood can induce the disintegration of the sleeve (=bio-degradation, decomposition in the body), provided that the sleeve is made of biodegradable polymers.

For blood vessel application, the active agent is preferably an antiproliferative agent such as sirolimus, or other limus derivatives or paclitaxel.

For use as a fallopian tube active agent with long-term contraceptive activity, the active agent is preferably a long-term stable depot gestagen, such as etonogestrel, levonorg-estrel, or a suitable antiprogesterone, such as mifepristone, or a spermicide, such as nonoxinol 9, or a combination thereof.

For use as carcinoma therapy in hollow organs, e.g., bile ducts, the active agent is preferably a cytostatic agent, such as mitomycin, capecitabine, or methotrexate (MTX).

When the sleeve is released from the balloon catheter, contact of the outer and inner surfaces with body fluid or blood induces the degradation process.

Figure 5:
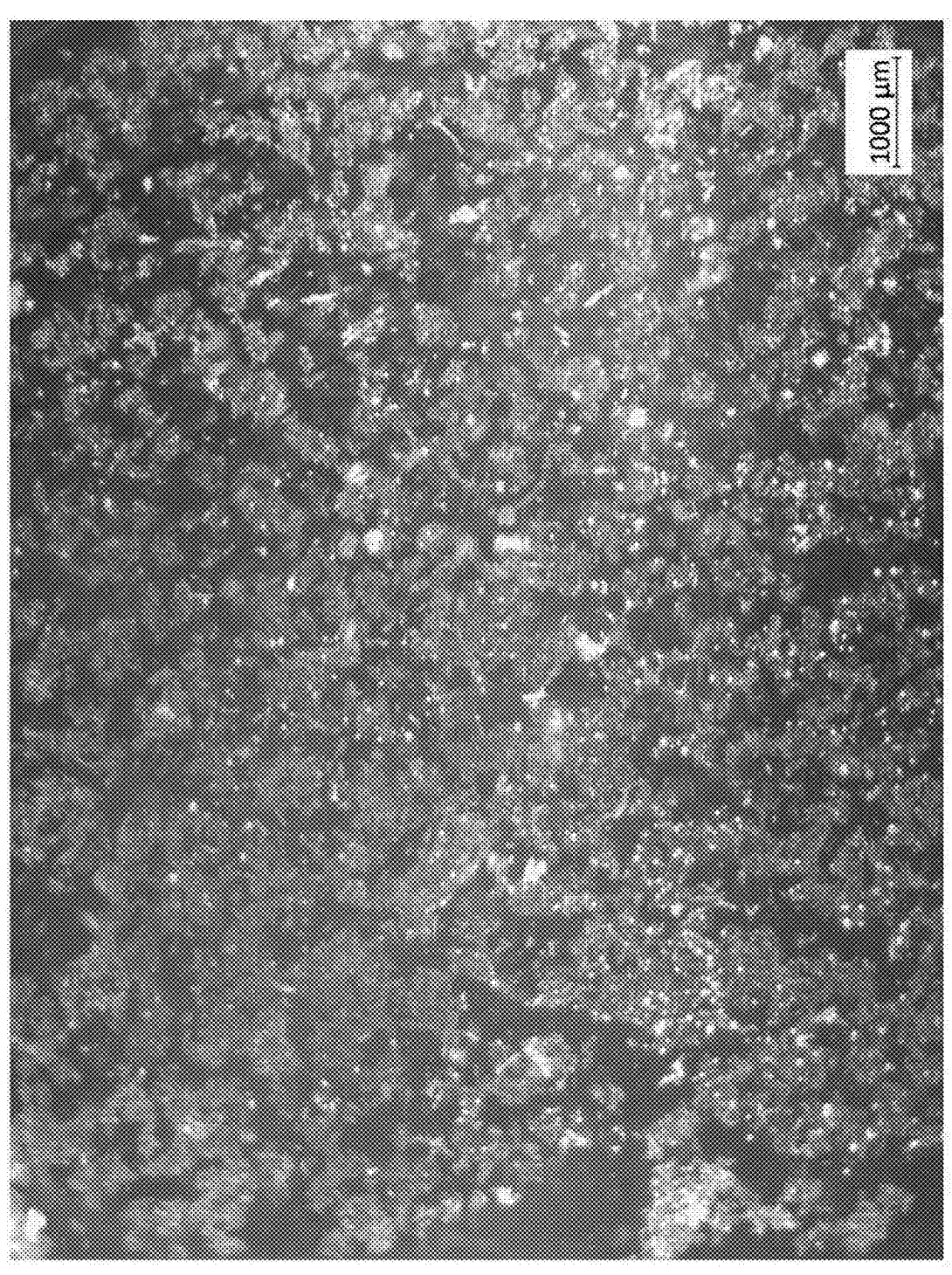
FIG. 5 is a microscopic image of the dissolution of the nonwoven after one day, where the size of the flakes corresponds to a nonwoven structure with a very low fraction of rapidly degradable polymer.
Figure 6:
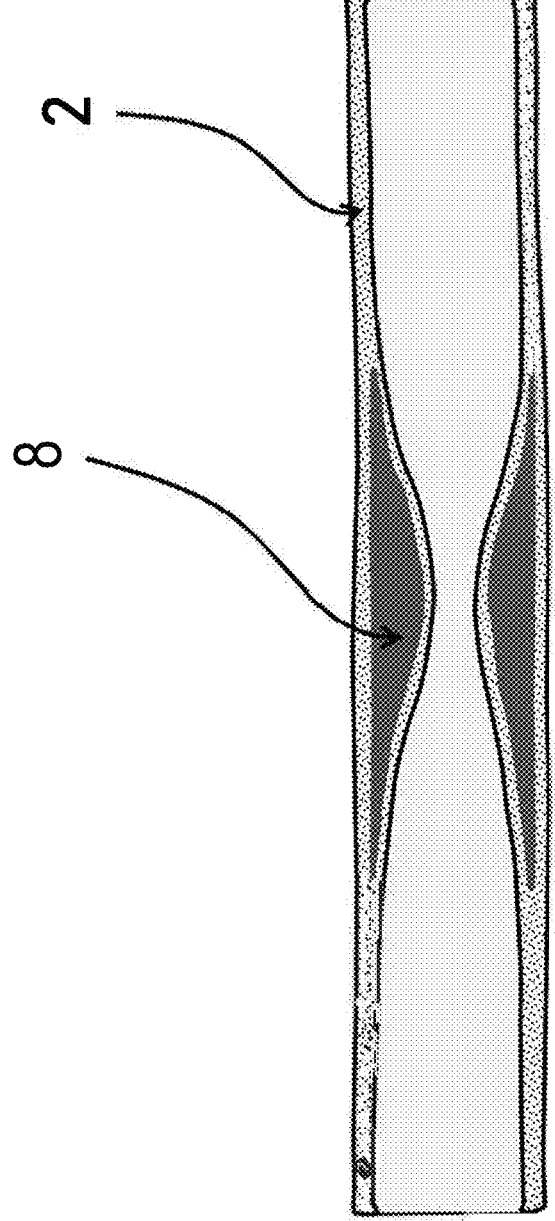
FIG. 6 is a schematic representation of an atherosclerotic narrowing in an artery.

In the case of the rapidly degradable component, rapid disintegration occurs. This rapid disintegration (within a few seconds up to 5 minutes) can cause fragmentation of the previously consistent cylindrical sheath into multiple "flakes" (=microparticles or "microflakes"), which are flat and adhere to the hollow organ wall (e.g. microscopy FIG. 5).

The size of the flakes depends on the degradation kinetics of the two polymers and on their mixing ratio. The exact degradation kinetics in blood or other body fluids can be adjusted and depends on the type of polymer, the molecular weight and the type of side chains (hydrophilic or hydro-phobic).

The nonwoven structure can have the following features in addition and/or as an alternative to the above features.

The approximately polygonal interspaces or microcom-partments between the individual polymer nanofibers have a maximum width of less than 100 μm, or less than 80 μm, or less than 60 μm, or less than 40 μm, or less than 30 μm, or less than 10 μm, and preferably less than 20 μm. The specified values can also refer to a maximum extension in the longitudinal direction of an elliptical or otherwise formed interspace, in which case the values relate to the widest width of the interspaces.

The tubular sleeve can also be doped with a hydrogel layer for adhesive bonding. The hydrogel layer preferably has a thickness of approx. 5 μm to 20 μm, or of 7.5 to 12.5 μm and in particular of 10 μm.

By doping the outer surface of the sleeve with a hydrogel layer, the sleeve adheres to an inner wall of a hollow organ, in particular a blood vessel, due to the hydrogel layer after deployment.

In addition, a biocompatible adhesive, such as a hydrogel, can stabilize the folded state of the sleeve during transport on the balloon catheter to the implantation site.

A nonwoven is a structure of fibers of limited length, continuous fibers (filaments) or chopped yarns of any type and origin, which have been joined together in some way to form a nonwoven (a fiber sheet, a fiber pile) and bonded together in some way.

Nonwovens are for the most part flexible textile sheets, i.e. they are easily bendable, their main structural elements are textile fibers and they have a comparatively small thickness compared to their length and width. There are also nonwovens which, because of the fibers used or the bonding processes, are more similar to papers, films or fiber-rein-forced plastics than to textiles. Nonwovens represent a material group with a wide variety of properties that can be specifically adapted to a broad spectrum of medical appli-cation requirements.

Furthermore, the sleeve can be cylindrical. Alternatively, the sleeve can also have any shape known from the stent domain. I.e. the sleeve can be conical, branched, constricted (in the manner of an egg timer), elliptical or circular in a side view.

The material from which the sleeve is formed, and its coating, preferably exhibit a certain compliance or conform-ability to conform to the structure of a wall or the surface texture of a hollow organ, and in this way cover lesions.

When the sleeve is released from the balloon catheter, contact of the outer and inner surfaces with body fluid or blood induces the degradation process.

Adhesion of the substances can be improved by surface structuring or gel film deposition of the surfaces of the sleeve.

The invention claimed is:

1. Tubular nonwoven structure as a carrier of an active agent, hereinafter referred to as a tubular sleeve, for atraumatic treatment of hollow organs, for application via a balloon catheter, wherein the tubular sleeve is folded about a longitudinal sleeve axis in an initial state and can be unfolded in a final state for attachment to an inner wall of a hollow organ, and the folding of the tubular sleeve is directed as pleating around the longitudinal sleeve axis, wherein the tubular sleeve is formed of areal zones comprising a plurality of first biodegradable polymer nanofibers and areal zones comprising a plurality of second biodegradable polymer nanofibers, wherein a medicinal active agent is incorporated into the plurality of first biodegradable polymer nanofibers and/or is arranged in interspaces between the plurality of first biodegradable polymer nanofibers, and wherein the areal zones comprising the plurality of first biodegradable polymer nanofibers are formed in such a way that the plurality of first biodegradable polymer nanofibers degrades over an adjustable period of time of 2 weeks to 3 months so that the active agent can be delivered to a hollow organ wall in this period of time, and the plurality of first biodegradable polymer nanofibers degrades more slowly than the plurality of second biodegradable polymer nanofibers, and the areal zones comprising the plurality of first biodegradable polymer nanofibers form microflakes which are in coherence with the areal zones comprising the plurality of second biodegradable polymer nanofibers.

2. Tubular sleeve according to claim 1, wherein the plurality of second biodegradable polymer nanofibers or further polymer nanofibers are formed such that the polymer nanofibers degrade over an adjustable period of time of 1 second to 2 weeks.

3. Tubular sleeve according to claim 1, wherein a biocompatible polymer of the first polymer nanofibers consists of polymers based on at least one of the group consisting of: lactic acid (polylactide, PLA), glycolic acid (polyglycolide, PGA) and their copolymers (poly (lactide-co-glycolide), PLGA), poly (ε-caprolactone), polyethylene glycol, polyethylene oxide, polysebacic acid, poly (trimethylene carbonate), poly (ethylene-co-vinyl acetate), poly (1,5-dioxepan-2-one), polyvinylpyrrolidone (PVP), poly-p-dioxanone (PPDX) and their compounds and copolymers or mixtures thereof, the polymer nanofibers having a fiber diameter in a range from 300 to 2000 nm.

4. Tubular sleeve according to claim 1, wherein the tubular sleeve is provided with a medical agent comprising at least one of the group consisting of an antiproliferative agent, a long-term stable depot gestagen, an antiprogesterone, a spermicide, and cytostatic agents.

5. Tubular sleeve according to claim 4, wherein the antiproliferative agent is sirolimus or other limus derivatives or paclitaxel (PTX);

the long-term stable depot gestagen is etonogestrel or levonorgestrel; the antiprogesterone is mifepristone; the spermicide is nonoxinol 9; and the cytostatic agents are mitomycin, capecitabine or methotrexate (MTX).

6. Tubular sleeve according to claim 1, wherein the tubular sleeve comprises a radial support layer formed by polymer nano-fibers with higher strength and/or by an additional polymer layer.

7. Tubular sleeve according to claim 6, wherein the additional polymer layer is a laser-cut tubular degradable polymer semi-finished product, or a layer formed by Melt Electrospinning Writing.

8. Tubular sleeve according to claim1, wherein at least an outer circumferential wall of the tubular sleeve has adhesive properties and/or is provided with a coating such that the circumferential wall adheres to an inner wall of a hollow organ during unfolding.

9. Method of producing the tubular sleeve according to claim 1, comprising the following steps:

providing a mixture of at least one polymer dissolved in a solvent and a medicinal agent, i.) applying the mixture layer by layer to a cylindrical support to form a tubular nonwoven sleeve of polymer nanofibers, pleating, folding and coiling the tubular sleeve in the same direction about the longitudinal axis after removal of the support, and mounting the tubular sleeve onto a balloon of a balloon catheter, or ii.) applying the mixture layer by layer directly to a support in the form of an inflated balloon of a balloon catheter to which a separation layer has previously been applied to form a tubular nonwoven sleeve of polymer nanofibers, and pleating, folding and winding the tubular sleeve together with the balloon membrane of the balloon catheter after deflation of the balloon.

10. Method according to claim 9, wherein the application of the solution to the cylindrical support or directly to the balloon is carried out by at least one of the group consisting of: spraying with an air jet (air spraying), spinning in an electric field (electrospinning), a combination of spraying with an air jet and spinning in an electric field (electrostatic air spraying), dipping in a solution (dip coating), applying a continuous melt strand (melt electrospinning writing), and applying discontinuously using 3D printing.

11. Method according to claim 9, wherein substances with a sufficiently high vapor pressure are provided as solvents for the mixture by spraying or electrospinning.

12. Method according to claim 9, wherein a first slowly degradable polymer is dissolved in a first solvent, or a solvent mixture of two or more solvents, and a second rapidly degradable polymer is dissolved in the first solvent or in a second solvent, or in a second solvent mixture of two or more solvents.

13. Method according to claim 9, comprising adding a protective colloid to the mixture, which improves the mixing and prevents the water-insoluble medicinal agent from separating, wherein the protective colloid is a rapidly soluble polymer.

14. Method according to claim 9, comprising applying a separation layer to the support prior to the application of the mixture.

15. Method according to claim 9, comprising introducing intermittent longitudinal cuts into the tubular sleeve prior to pleating and folding, wherein the pleating and folding of the tubular nonwoven sleeve can be guided and facilitated by the intermittent longitudinal slits.

16. The method according to claim 9, wherein the carrier support is a cylindrical support body or an inflated balloon.

17. The method according to claim 9, wherein the tubular nonwoven sleeve is pleated and folded together with the balloon membrane of the balloon catheter and wrapped around a catheter shaft.

18. The method according to claim 9, comprising applying the separation layer to an outer surface of the inflated balloon of the balloon catheter, and then applying the tubular sleeve onto the separation layer.

* * * * *